(12) United States Patent
Walker et al.

(10) Patent No.: US 10,603,486 B2
(45) Date of Patent: Mar. 31, 2020

(54) NEURAL INTERFACE FABRICATION

(71) Applicant: GALVANI BIOELECTRONICS LIMITED, Brentford, Middlesex (GB)

(72) Inventors: Dwight Sherod Walker, Durham, NC (US); Daniel John Chew, Middlesex (GB)

(73) Assignee: GALVANI BIOELECTRONICS LIMITED, Brentford, Middlesex (GB)

( * ) Notice: Subject to any disclaimer, the term of this patent is extended or adjusted under 35 U.S.C. 154(b) by 0 days.

(21) Appl. No.: 16/309,182

(22) PCT Filed: Jun. 12, 2017

(86) PCT No.: PCT/US2017/037010
§ 371 (c)(1),
(2) Date: Dec. 12, 2018

(87) PCT Pub. No.: WO2017/218413
PCT Pub. Date: Dec. 21, 2017

(65) Prior Publication Data
US 2019/0247645 A1    Aug. 15, 2019

Related U.S. Application Data

(60) Provisional application No. 62/382,918, filed on Sep. 2, 2016, provisional application No. 62/349,388, filed on Jun. 13, 2016.

(51) Int. Cl.
*B29C 43/18* (2006.01)
*A61N 1/05* (2006.01)
(Continued)

(52) U.S. Cl.
CPC ........ *A61N 1/0556* (2013.01); *A61B 5/04001* (2013.01); *A61B 5/6846* (2013.01); *B29C 43/18* (2013.01); *B29C 2043/182* (2013.01)

(58) Field of Classification Search
None
See application file for complete search history.

(56) References Cited

U.S. PATENT DOCUMENTS 6,600,956 B2    7/2003  Maschino
6,982,232 B2    1/2006  Borrelli et al.
(Continued)

FOREIGN PATENT DOCUMENTS

WO    WO 2007/024323 A2    3/2007
WO    WO 2008/025155 A1    3/2008
(Continued)

OTHER PUBLICATIONS

International Search Report and Written Opinion dated Oct. 15, 2018 issued in PCT/US2017/037010.
(Continued)

*Primary Examiner* — Edmund H Lee
(74) *Attorney, Agent, or Firm* — Scully, Scott, Murphy & Presser, P.C.

(57) ABSTRACT

Methods for fabricating implantable cuff electrodes for contacting or at least partially surrounding internal body tissue such as, e.g., nerves, smooth muscles, striated muscles, arteries, veins, ligamental tissues, connective tissues, cartilage tissues, bones, or other similar body tissues, structures and organs are disclosed. An example method includes preparing a substrate including an implantable cuff electrode shape, applying a mold material to the substrate, curing the mold material to form a mold, releasing the mold from the substrate, inserting at least one conductor into the mold that penetrates through the channel of the mold, pressing a formable material into the channel of the mold to form a body of an implantable cuff electrode about the at (Continued)

least one conductor, curing the body of the implantable cuff electrode, and releasing the body of the implantable cuff electrode from the mold.

15 Claims, 5 Drawing Sheets

(51) Int. Cl.
*A61B 5/04* (2006.01)
*A61B 5/00* (2006.01)

(56) References Cited

U.S. PATENT DOCUMENTS

| | | | |
|---|---|---|---|
| 7,397,631 B1 | 7/2008 | Suwito et al. | |
| 7,618,577 B2 | 11/2009 | Fawcett, Jr. et al. | |
| 7,797,058 B2* | 9/2010 | Mrva | A61N 1/0556 |
| | | | 606/129 |
| 7,996,092 B2* | 8/2011 | Mrva | A61N 1/0556 |
| | | | 607/118 |
| 8,128,393 B2 | 3/2012 | Rolland et al. | |
| 8,214,056 B2* | 7/2012 | Hoffer | A61N 1/0556 |
| | | | 607/118 |
| 8,214,057 B2* | 7/2012 | Barolat | A61B 5/04001 |
| | | | 607/117 |
| 8,428,749 B2* | 4/2013 | Hoffer | A61N 1/0556 |
| | | | 607/118 |
| 8,600,518 B2* | 12/2013 | Meadows | A61N 1/05 |
| | | | 600/373 |
| 8,983,626 B2 | 3/2015 | Zarembo et al. | |
| 9,340,001 B2 | 5/2016 | Rolland et al. | |
| 9,352,421 B2 | 5/2016 | Illston | |
| 10,226,317 B2* | 3/2019 | Deitch | A61F 2/004 |
| 2006/0030919 A1* | 2/2006 | Mrva | A61N 1/0556 |
| | | | 607/118 |
| 2008/0065184 A1* | 3/2008 | Hoffer | A61N 1/0556 |
| | | | 607/118 |
| 2010/0047376 A1* | 2/2010 | Imbeau | A61N 1/0556 |
| | | | 425/116 |
| 2010/0168831 A1* | 7/2010 | Korivi | A61N 1/0556 |
| | | | 607/118 |
| 2010/0298920 A1* | 11/2010 | Mrva | A61N 1/0556 |
| | | | 607/118 |
| 2013/0085359 A1 | 4/2013 | Yao et al. | |
| 2015/0072163 A1 | 3/2015 | Fukushima | |
| 2016/0276056 A1 | 9/2016 | Stolyarov et al. | |

FOREIGN PATENT DOCUMENTS

| | | |
|---|---|---|
| WO | WO 2013/036988 A1 | 3/2013 |
| WO | WO 2014/189371 A2 | 11/2014 |
| WO | WO 2015/012469 A1 | 1/2015 |

OTHER PUBLICATIONS

Xia, Y. et al., "Soft Lithography", Angew. Chem. Int. Ed. (1998), vol. 37, pp. 550-575.

* cited by examiner

NEURAL INTERFACE FABRICATION

CROSS-REFERENCE TO RELATED APPLICATIONS

The present invention claims the benefit of U.S. Provisional Patent Application Ser. No. 62/349,388 filed Jun. 13, 2016 and U.S. Provisional Patent Application Ser. No. 62/382,918 files Sep. 2, 2016, the entire content and disclosure of each of which is incorporated herein by reference.

TECHNICAL FIELD

Methods of fabricating neural interfaces for use in at least one of the detection, stimulation, and recording of electrical, chemical, and ionic interactions between a neural interface and various biologic and chemical targets are described.

BACKGROUND OF THE INVENTION

The developing field of neural stimulation and recording generally involves the application or measurement of electrical signals associated with nerves and muscles to induce or measure specific physiological responses. The field has developed to support a variety of applications, including, but not limited to, neuromuscular control, optical prostheses, pain therapy, and morbid obesity treatment. In this field, "cuff" electrodes which may contact, engage, or partially or completely surround a nerve fiber or branch to be stimulated or monitored, may often be used. The use of neural stimulation and recording in such situations provides a minimally invasive, reversible treatment requiring minimal post-operative care as opposed to highly invasive, non-reversible and expensive surgical alternatives.

Neural stimulation and recording techniques for controlling, interpreting and treating numerous pathological conditions may utilize a periodic or constant electrical stimulation or reading of specific nerves, nerve fibers and muscles by one or more electrodes. Numerous electrode designs have been developed to date for applications involving functional electrical stimulation of nerves and nerve fibers. One of the most commonly employed electrode designs is the cylindrical cuff electrode. This design is simple and relatively easy to use for long term use in subjects even when they are moving. Cylindrical cuff electrodes are well suited for use with nerves due to the geometry of a typical nerve or nerve fiber, which is considered to be cylindrical from a design perspective. Some examples of cuff electrodes may be found in U.S. Pat. Nos. 6,600,956, and 8,983,626, and U.S. Patent Application Publication Nos. 2013/0085359 and 2010/0168831 the entire content and disclosure of each of which is incorporated herein by reference. One of the barriers to widespread use of these cuff electrodes is the lack of fabrication techniques that provide scalable commercial production. Existing cuff electrodes are generally fabricated only at a scale suitable to larger nerves and muscles and many cuff electrodes are designed based on components that would be difficult or impossible manufacture at a highly reduced scale for fitment to small nerves and muscles.

As an example, one of the current methods of manufacturing cuff electrodes is through manual casting. Manual casting produces small production quantities and does not generally lend itself to mass fabrication of reduced scale cuff electrodes.

Alternate manufacturing techniques of fabrication processes for implantable neural interface devices may include, for example, additive manufacturing, stamping, casting, injection molding, photolithography, and subtractive manufacturing, however each of these has drawbacks.

Additive Manufacturing

Additive manufacturing describes a process where a part or parts are formed by accumulating and fusing material together, typically in a layer-on-layer manner that builds 3D objects by adding layer-upon-layer of material, whether the material is plastic, metal, concrete or human tissue. Common additive manufacturing technologies may include or utilize features such as computers, 3D modeling software, machine equipment, and layering material. The term additive manufacturing encompasses many technologies and may include subsets such as, for example, 3D Printing, Rapid Prototyping (RP), Direct Digital Manufacturing (DDM), layered manufacturing and additive fabrication. See, e.g., U.S. Pat. No. 9,352,421, U.S. Patent Publication No. 2016/0276056, and International Patent Application Publication WO2015/012469 the entire content and disclosure of each of which is incorporated herein by reference. The use of additive manufacturing techniques like 3-D printing produces cuffs at a low rate, similar to that of manual casting, and does not generally lend itself to mass fabrication of reduced scale cuff electrodes.

Stamping

Stamping (also known as pressing) is the process of placing flat sheet material in either blank or coil form into a stamping press where a tool and die surface forms the material into a net shape. Stamping includes a variety of sheet-material forming manufacturing processes, such as, for example, punching using a machine press or stamping press, blanking, embossing, bending, flanging, and coining. A stamping process is usually carried out on sheet metals, but can also be used on other materials, such as polymers. Examples of applications of sheet material stamping include electrical connectors, micromeshes, microswitches, microcups, wristwatch components, handheld device components, and medical devices. See, e.g., U.S. Pat. No. 7,397,631 the entire content and disclosure of which is incorporated herein by reference.

Casting

Casting is a manufacturing process in which a liquid material is usually poured into a mold, which contains a hollow cavity of the desired shape, and then allowed to solidify. The solidified part is also known as a casting, which is ejected or broken out of the mold to complete the process. Casting materials are usually metals or various cold setting materials that cure after mixing two or more components together. Some examples of casting materials include epoxy, concrete, plaster, ceramic and clay. Casting is most often used for making complex shapes that would be otherwise difficult or uneconomical to make by other methods. See, e.g., U.S. Patent Application Publication No. 2015/0072163 the entire content and disclosure of which is incorporated herein by reference.

Role to Role Printing

Roll-to-roll printing, also known as web printing, reel-to-reel processing or R2R, is the process of creating electronic devices on a roll of flexible plastic or metal foil. In other fields predating this use, it can refer to any process of applying coatings, printing, or performing other processes starting with a roll of a flexible material and re-reeling after the process to create an output roll. These processes can be grouped together under the general term converting. When the rolls of material have been coated, laminated or printed they are normally slit to their finished size on a slitter rewinder. See, e.g., U.S. Pat. Nos. 8,128,393 and 9,340,001 the entire content and disclosure of each of which is incorporated herein by reference.

Injection Molding

Injection molding is a manufacturing process for producing parts by injecting material into a mold. Injection molding can be performed with a host of materials, including metals, (for which the process is called die-casting), glasses, elastomers, confections, and most commonly thermoplastic and thermosetting polymers. Material for the part is fed into a heated barrel, mixed, and forced into a mould cavity, where it cools and hardens to the configuration of the cavity. Molds are generally made from metal, usually either steel or aluminum, and precision-machined to form the features of the desired part. Injection molding is widely used for manufacturing a variety of parts, from the smallest components to entire body panels of cars. See, e.g., U.S. Pat. No. 7,618,577 the entire content and disclosure of which is incorporated herein by reference.

Photolithography

Photolithography, also termed optical lithography or UV lithography, is a process used in microfabrication to pattern parts of a thin film or the bulk of a substrate. It uses light to transfer a geometric pattern from a photomask to a light-sensitive chemical "photoresist", or simply "resist", on the substrate. A series of chemical treatments then either engraves the exposure pattern into, or enables deposition of a new material in the desired pattern upon, the material underneath the photo resist. For example, in complex integrated circuits, a modern CMOS wafer will go through the photolithographic cycle up to 50 times. See, e.g., U.S. Pat. No. 6,982,232 the entire content and disclosure of which is incorporated herein by reference.

Subtractive Manufacturing

Subtractive manufacturing, often referred to as machining, is any of various processes in which a piece of raw material is cut into a desired final shape and size by a controlled material-removal process. The processes that have this common theme, controlled material removal, are today collectively known as subtractive manufacturing, in distinction from processes of controlled material addition, which are known as additive manufacturing. Exactly what the "controlled" part of the definition implies can vary, but it almost always implies the use of machine tools (in addition to just power tools and hand tools). Subtractive manufacturing is a part of the manufacture of many metal products, but it can also be used on materials such as wood, plastic, ceramic, and composites. See, e.g., International Patent Application Publication WO2014/189371 the entire content and disclosure of which is incorporated herein by reference.

SUMMARY

Methods of fabricating implantable electrode cuffs are disclosed. In some aspects, a method includes preparing a substrate including an implantable cuff electrode shape, applying a mold material to the substrate and curing the mold material to form a mold. The mold may include a channel defined by the implantable cuff electrode shape of the substrate. The method further includes releasing the mold from the substrate and inserting at least one conductor into the mold. The at least one conductor may penetrate through the channel of the mold. The method further includes pressing a formable material into the channel of the mold to form a body of an implantable cuff electrode. The body may be formed about the at least one conductor penetrating through the channel of the mold. The method further includes curing the body of the implantable cuff electrode and releasing the body of the implantable cuff electrode from the mold.

In an aspect, the formable material may be pressed into the channel by at least one roller. In a further aspect, the at least one roller may be heated.

In another aspect, the body of the implantable cuff electrode is formed with an opening extending therethrough. The opening may be configured to receive a portion of internal body tissue therethrough.

In an aspect, the portion of internal body tissue that the opening is configured to receive is selected from the group consisting of nerves, smooth muscles, striated muscles, arteries, veins, ligamental tissues, connective tissues, cartilage tissues, bones, or other similar body tissues, structures and organs.

In another aspect, the body of the implantable cuff electrode includes a channel extending from an exterior surface of the body into the opening. The channel of the body may be configured to allow passage of the portion of internal body tissue therethrough to the opening.

In yet another aspect, a cross-sectional region of the opening defines a shape selected from the group consisting of a circular shape, an oval shape, a triangular shape, a pentagonal shape, a square shape, a rectangular shape, a star shape, and a hexagonal shape.

In an aspect, a cross-sectional region of the opening may have a diameter between about 0.001 mm and about 12 mm. In a further aspect, the cross-sectional region of the opening may have a diameter between about 0.01 mm and about 10 mm. In a yet a further aspect, the cross-sectional region of the opening may have a diameter between about 0.1 mm and about 10 mm. In a further aspect, the cross-sectional region of the opening may have a diameter between about 0.5 mm and about 10 mm.

In an aspect, the opening may be shaped such that the outer surface of the opening contacts the internal body tissue.

In another aspect, the formable material may be a high volume resistivity material having a resistivity greater than about $1 \times 10^{22}$ $\Omega$-cm.

In yet another aspect, the formable material may be a material selected from the group consisting of paralene-C, silicone, Teflon, polyimide, PDMS, SU-8 and liquid crystal polymers.

In another aspect, the cured body of the implantable cuff electrode may have a flexural rigidity of less than about $1 \times 10^{-12}$ N-m$^2$.

In an aspect, the at least one conductor may be selected from the group consisting of titanium nitride, platinum, platinum-iridium alloys, gold, hydrogel, iridium oxide, silicon carbide, stainless steel and graphene, carbon fibers, carbon nanotube structures, Tantalum, $Ta_2O_5$, PEDOT and conducting polymers.

In some aspects, a method for fabricating an implantable cuff electrode is disclose including providing a fluorinated elastomer-based material. The fluorinated elastomer-based material may include a first surface defining a plurality of channels. Each channel of the plurality of channels may define an implantable cuff electrode shape and may be less than about 5 millimeters in a largest dimension. The layer of fluorinated elastomer-based materials may be less than about 10 millimeters in thickness. The method may further includes bonding a support layer to a second surface of the fluorinated elastomer-based material opposite the first surface and dispensing a curable material on at least a portion of the first surface of the fluorinated elastomer-based material. The curable material may be configured to conform to the channels defined in the first surface of the fluorinated elastomer-based material. The method may further include positioning a film proximate to the first surface of the fluorinated elastomer-based material. The curable material may be disposed between the film and the first surface of the fluorinated elastomer-based material. The method may further include positioning the fluorinated elastomer-based material, curable material, support layer and film between a first roller and a second roller. The first and second rollers may define a nip point to press the curable material into the channels. The method may further include applying pressure to the curable material using the first and second rollers to fill the channels with the curable material.

In an aspect, the method may further include disposing a tie-layer between the fluorinated elastomer-based material and the support layer to attach the support layer to the fluorinated elastomer-based material.

In an aspect, the fluorinated elastomer-based material may be attached to the support layer by at least one of a photoinitiator coupling and a thermalinitiator coupling.

In an aspect, the first roller and second roller may be configured and dimensioned to pinch the fluorinated elastomer-based material, the support layer, the sheet, and the curable material therebetween when the fluorinated elastomer-based material, the support layer, the sheet, and curable material are positioned between the first and second rollers.

Any of the above aspects may be combined without departing from the scope of the present disclosure.

DEFINITIONS

Figure 1:
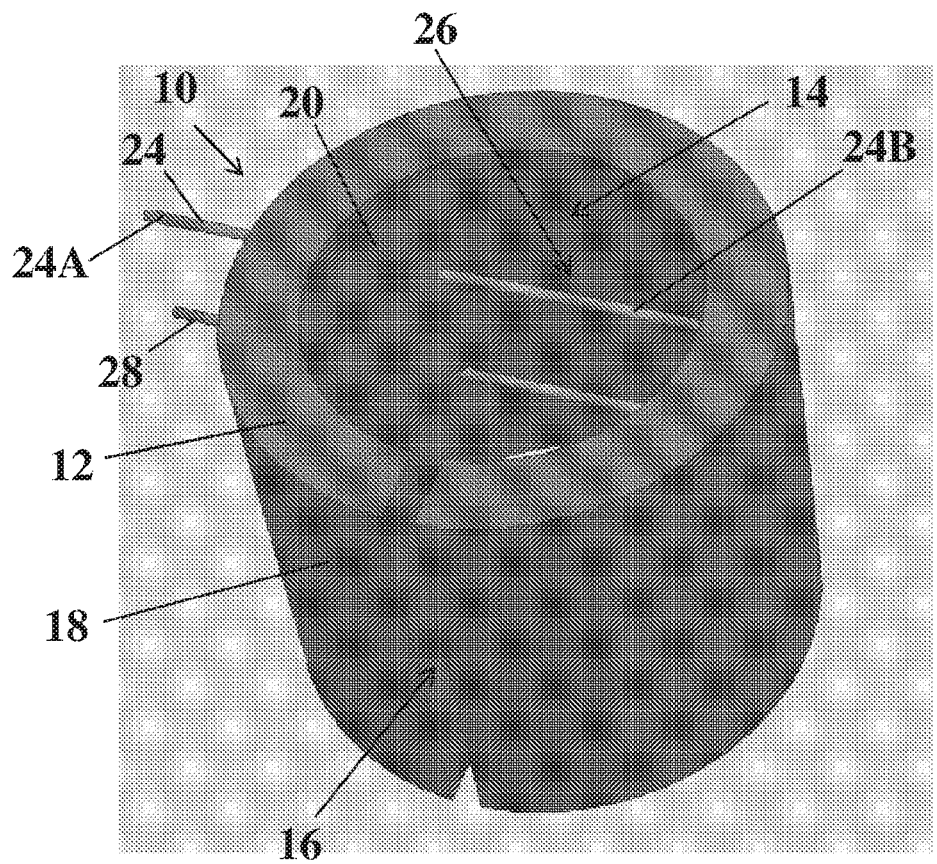
FIG. 1 is an isometric view of an implantable cuff electrode according to an aspect of the present disclosure.

The following definitions form the basis for the written description and the claims:

The singular forms "a", "an", and "the" include plural references unless the context clearly dictates otherwise. Thus, for example, reference to "an array" includes reference to one or more of such materials and reference to "subjecting" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, the recitation of a numerical range for a variable is intended to convey that the variable may be equal to any of the values within that range. Thus, for a variable which is inherently discrete, the variable may be equal to any integer value in the numerical range, including the end-points of the range. Similarly, for a variable which is inherently continuous, the variable may be equal to any real or imaginary value of the numerical range, including the endpoints of the range. As an example, a variable which is described as having values between 0 and 2, may include 0, 1 or 2 for variables which are inherently discrete, and may include 0.0, 0.1, 0.01, 0.001, or any other real or imaginary value for variables which are inherently continuous.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

In the present disclosure, the term "preferably" or "preferred" is non-exclusive where it is intended to mean "preferably, but not limited to". Any steps recited in any method or process claims may be executed in any order and are not limited to the order presented in the claims. Means-plus function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Methods of Manufacturing

Replica Printing

Imprint lithography techniques, for example, as described in Xia, Y., et al., Angew. Chem. Int. Ed., 1998, 37, 550-575, may include methods such as, for example, solvent-assisted micro-molding (SAMIM), micro-molding in capillaries (MIMIC), and microcontact printing (MCP), and may often be referred to as soft lithographic techniques. Discrete micro and nanoscale objects may be formed in predetermined shapes and sizes and predetermined size dispersions. The objects may also be attached to a film to form arrays of objects on a film. The objects may be formed from molding techniques that may include high throughput and continuous particle molding. See, e.g., International Patent Application WO2007/024323 the entire content and disclosure of which is incorporated herein by reference.

In some aspects, some of the features and techniques of replica printing may be utilized to address the need for a manufacturing method that retains the design detail while allowing for a reduction in overall size and an increase the number of objects produced. For example, a detailed replica of the original object to be formed may be produced by a number of means including lithographic techniques, providing nanometer scale resolution, while also being able to form a plurality of detailed replicas of the original object. The combination of the detail provided by the original object and the production of a plurality of detailed replica objects makes replica printing an accurate and scalable technique.

DETAILED DESCRIPTION

In some aspects, methods for fabricating an implantable cuff electrode are disclosed. The implantable cuff electrode may be used, for example, to contact or at least partially surround internal body tissue such as, e.g., nerves, smooth muscles, striated muscles, arteries, veins, ligamental tissues, connective tissues, cartilage tissues, bones, or other similar body tissues, structures or organs.

Figure 2:
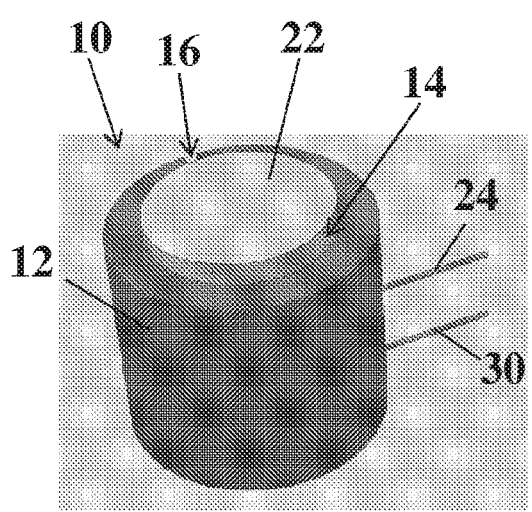
FIG. 2 is an isometric view of the cuff of FIG. 1, taken from another angle and including an illustration of a portion of an internal body tissue positioned within an opening of the cuff.
Figure 3:
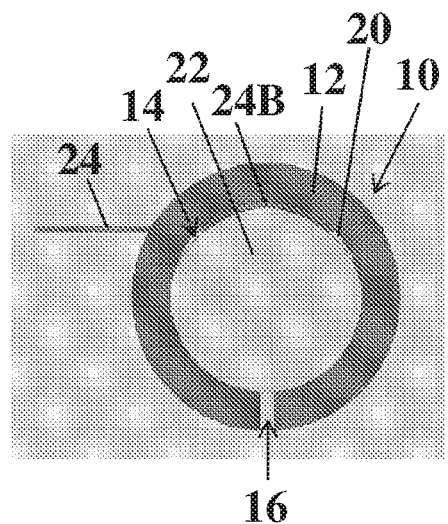
FIG. 3 top plan view of the cuff of FIG. 2, illustrating the engagement of the portion of the internal body tissue against conductors of the cuff in the opening of the cuff.

With reference now to FIGS. 1-3, an example implantable cuff electrode 10 is illustrated. In some aspects, cuff 10 may include a body 12 and an opening 14 that extends through the body 12. For example, opening 14 may be a through-hole extending through the body 12 of cuff 10 in a longitudinal direction. Opening 14 may be configured to receive a portion of an internal body tissue 22, for example, a nerve, therethrough when cuff 10 is implanted.

In some aspects, body 12 may define a circular cross-section. In some aspects, body 12 may define any other cross-section that is capable of receiving the portion of internal body tissue 22 through an opening 14 extending therethrough. For example, in some aspects, body 12 may define a polygonal cross-section, e.g., oval, triangular, square, rectangular, pentagonal, hexagonal, star-shaped, or may define any other cross-section that may receive the portion of internal body tissue 22 through an opening 14.

In some aspects, the size of opening 14 and cuff 10 may be defined based on a target portion of internal body tissue 22. For example, in some aspects, the dimensions of opening 14 and cuff 10 may be determined such that the diameter of opening 14 is greater than the outer diameter of the portion of body tissue 22. In some aspects, for example, the opening 14 may have a diameter between about 0.001 and about 12 mm. In some aspects, for example, the opening 14 may have a diameter between about 0.01 and 10 mm. In some aspects, for example, the opening 14 may have a diameter between 0.1 and 10 mm. In some aspects, for example, the opening 14 may have a diameter of between about 0.5 and 10 mm.

In some aspects, cuff 10 may include a channel 16 extending through body 12 from an exterior surface 18 of body 12 to an interior surface 20 of body 12. In some aspects, for example, channel 16 may extend through body 12 and into opening 14. In some aspects, channel 16 may extend the entire length of body 12 in the longitudinal direction such that body 12 may only form a partial circle or other cross-sectional shape. For example, in some aspects, the portion of internal tissue 22 may be received into opening 14 through channel 16 during implantation of cuff 10. In some aspects, for example, cuff 10 may be manipulated using one or more manipulator tools (not shown) such as a needle or other tool. In some aspects, for example, a portion of exterior surface 18 of cuff 10, for example, a portion proximate to channel 16, may include one or more pockets (not shown) for receiving a portion of the needle or tool to allow the needle or tool to control the portions of the cuff 10 proximate to channel 16. In some aspects, once the cuff 10 is positioned around a portion of internal tissue, tissue growth around the cuff 10 may further secure the cuff 10 in place. In some aspects, a proximal portion, distal portion, or any other portion of cuff 10 proximate channel 16 may be manipulated to reversibly or irreversibly close at least apportion of channel 16. For example, in some aspects, an adhesive may be applied to a portion of the cuff 10 proximate to channel 16, e.g., on a wall of channel 16, and channel 16 may be pressed together to close the channel. As another example, in some aspects, the walls of channel 16 may be welded together. In yet another example, the walls of channel 16 or a portion of cuff 10 proximate channel 16 may be sutured together to close channel 16. Any other method of reversibly or irreversibly closing channel 16 may also be employed.

In some aspects, cuff 10 may be configured for use on smaller peripheral nerves, for example, on such nerves having a diameter of about 1 mm or less, and much smaller nerves, e.g., having a diameter down to about 100 μm or less. In some aspects, cuff 10 may be constructed for use with larger nerves having diameters of greater even than 1 mm if desired.

In some aspect, for example, cuff 10 may be attached to the carotid sinus nerve (CSN) in humans to block and treat type 2 diabetes. The CSN is approximately between 0.5 mm and 3 mm in diameter in humans so is difficult to provide an electrical connection to the CSN using commercially used and approved larger nerve cuffs. In some aspects, cuff 10 may be used on larger nerves including the vagus nerve in humans (approximately between 2 mm and 5 mm in diameter) that can be used to treat medical conditions such as, for example, epilepsy, depression, and tremors from rheumatoid arthritis.

In some aspects, cuff 10 may also be used for neuroprosthesis to restore movement by electrically stimulating nerves involved in motor control, for example by cuffing the sciatic nerve which has a diameter of approximately between 7 and 14 mm in humans. Disease applications may include, for example, correcting foot drop, and restoring walking after spinal cord injury. In some aspects, cuff 10 may also or instead be used to provide sensory feedback for control of robotic prostheses, such as artificial arms, hands or lower extremities, and for other uses in which electrical signals of the nerve are detected. In some aspects, cuff 10 may be used for conduction blocking peripheral nerves for treatment of phantom limb and pain. In some aspects, cuff 10 may also or alternatively be used on body tissues such as smooth muscle tissues to monitor, supply, inhibit, or prevent electrical signals in smooth muscles.

In some aspects, body 12 of cuff 10 may be formed of a formable or shape memory material. For example, body 12 may be flexible or deformable during insertion or implantation of cuff 10 into the body so that cuff 10 may be positioned surrounding the portion of internal tissue 22. For example, in some aspects, cuff 10 may include a first configuration substantially as illustrated in FIGS. 1-3 where channel 16 defines a relatively small opening as compared to a size of opening 14. In some aspects, body 12 of cuff 10 may be deformed to at least a second configuration (not shown) during implantation for receiving the portion of internal tissue 22 through channel 16. In some aspects, once the portion of internal tissue 22 is received through channel 16 and positioned within opening 14, cuff 10 may be returned to the first configuration to secure the cuff 10 about the portion of internal tissue 22 as illustrated, for example, in FIG. 2.

In some aspects, for example, cuff 10 may be biased toward the first configuration and a force may be required to be applied to the cuff 10 to transition the cuff 10 toward the second configuration. Once the portion of internal tissue 22 is received through channel 16 and positioned within opening 14, the force may be removed to allow the cuff 10 to transition back toward the first configuration due to the bias of the cuff.

In some aspects, for example, when the portion of internal tissue 22 is received within opening 14, channel 16 may be secured against release of the portion of internal tissue 22. For example, channel 16 may be secured against release of the portion of internal tissue using biasing forces, a flap (not shown), a door (not shown), a pin (not shown), a clip (not shown) or any other manner of securement. In some aspects, temporary or permanent securement of channel 16 may be achieved for example, through the use of adhesive, welding, suturing, or other similar techniques.

In some aspects, for example, body 12 may be formed of a high volume resistivity material. For example, the high volume resistivity material may be a material having a resistivity greater than $1 \times 10^{22}$ Ω-cm. Some example materials that may be used for body 12 may include paralene-C, silicone, shape memory polymers, Teflon, polyimide, PDMS, SU-8 and liquid crystal polymers.

In some aspects, body 12 may have a flexural rigidity of less than $1 \times 10^{-12}$ N-m².

In some aspects, cuff 10 may include a conductor 24 extending therethrough, for example, a wire, electrode, or any other conductor.

In some aspects, the conductor may be formed from, for example, titanium nitride, platinum, platinum-iridium alloys, gold, hydrogels, iridium oxide, silicon carbide, stainless steel and graphene, carbon fibers, carbon nanotube structures, Tantalum, $Ta_2O_5$, PEDOT and conducting polymers.

In some aspects, for example, conductor 24 may be formed of a conducting polymer created by electro polymerization occurring from nucleation sites. For example, during polymerization, the conducting polymer monomer may be oxidized under a positive voltage, the amplitude of which is dependent on the monomer, dopant, and electrolyte choice, to form oligomers which precipitate out of solution when the chain reaches a critical length. In the case of neural interface, conducting polymers may be grown within hydrogels to produce conductive hydrogels. For example, the introduction of (i) conductive bulk metallic glass (BMG) particles composed of Mg64Zn30Ca5Na1 and (ii) a dispersion of chemically synthesized poly(3,4-ethylene dioxythiophene)-poly(styrene sulfonate) (PEDOT: PSS) may yield suitable conductive hydrogels.

In some aspects, for example, conductor 24 may extend through cuff 10 in a direction transverse to the longitudinal direction of the cuff 10. In some aspects, conductor 24 may extend through cuff 10 perpendicular to the longitudinal direction of the cuff 10. In some aspects, conductor 24 may extend through cuff 10 in a direction parallel to the longitudinal direction of the cuff 10.

As illustrated in FIG. 1, in some aspects, conductor 24 may extend through opening 14 of cuff 10. For example, in some aspects, conductor 24 may extend through opening 14 adjacent or proximate to a portion of surface 20 of body 12 that is disposed opposite the channel 16. In some aspects, for example, a gap or space 26 may be defined in opening 14 between conductor 24 and surface 20.

In some aspects, conductor 24 may extend through the external surface 18 of cuff 10 on one side of cuff 10, through opening 14, and through the external surface 18 of cuff 10 on an opposite side of cuff 10. In some aspects, conductor 24 may only extend through the external surface 18 of cuff 10 on only one side of cuff 10, for example, as illustrated in FIGS. 1-3. For example, conductor 24 may include a portion 24A extending outside of cuff 10 from the external surface 18 on one side of cuff 10, and a portion 24B within opening 14 of cuff 10, e.g., extending between two portions of the internal surface 20 of cuff 10. In some aspects, the portion 24A outside of cuff 10 may be insulated, such as, e.g., a polymer or other coating, such as parylene, while the portion 24B inside of the opening 14 may be left un-insulated to facilitate the transmission and reception of signals from the portion of tissue received within opening 14.

In some aspects, conductor 24 may extend through any other portion of opening 14. In some aspects, for example, the portion of conductor 24B extending through opening 14 may be in contact with surface 20 of body 12. In some aspects, the portion of conductor 24 extending through opening 14 may be in continuous contact with the surface 20 of body 12, e.g., such that no gap or space 26 is present between conductor 24 and surface 20 of body 12.

In some aspects, more than one conductor may be present in cuff 10. For example, in addition to conductor 24, any number of additional conductors may also be present that have similar features to conductor 24. For example, as illustrated in FIGS. 1 and 2, at least a second conductor 28 may be included in cuff 10 and configured in any of the aspects described above for conductor 24. In some aspects, for example, conductor 24 and conductor 28 may have similar or different orientations or positions within cuff 10. In some aspects, for example, there may be 1, 2, 3, 4, 5, 6, 7, 8, 9, 10, or more conductors.

As illustrated in FIG. 3, when the portion of internal tissue 22 is received within opening 14, conductor 24 (and conductor 28 or any other conductor of cuff 10) may be engaged against or in contact with the portion of tissue 22. For example, when the portion of internal tissue 22 is received within opening 14, the portion of internal tissue 22 may engage against conductor 24 or otherwise contact conductor 24 and cause conductor 24 to move, bend, or stretch toward surface 20. For example, conductor 24 may conform to the shape of the portion of internal tissue 22. In some aspects, the engagement of the portion of internal tissue 22 with conductor 24 may cause conductor 24 to engage against surface 20, for example, a portion of surface 20 opposite channel 16, as illustrated in FIG. 3. Due to engagement with the portion of tissue 22, conductor 24 may receive, sense, detect or induce biological changes or signals through or to the portion of tissue internal 22.

In some aspects, a driving unit (not shown) may be implanted in the patient near the cuff 10 during use and electrically connected to conductor 24 or any other conductors of cuff 10. In some aspects, driving unit may be located outside of the patient and leads may extend from conductor 24 through the skin of the patient to the driving unit. In some aspects, conductor 24 may be connected to a wireless transmitter (not shown) for transmitting and receiving signals from a remote driving unit. In some aspects, a conductor 24 may also be electrically connected to a power source (not shown) such as, e.g., a battery. The driving unit may fulfill a variety of functions depending on the intended use of the cuff 10, for example by supplying one or more stimulation signals to the electrodes so as to stimulate the portion of internal tissue in some way, providing a stimulation signal to block signals on the portion of internal tissue, and/or reading one or more electrical signals from the portion of internal tissue.

In some aspects, conductor 24 may, for example, be formed of a flexible or semi-rigid material that may be biased toward a first configuration or state as illustrated in FIG. 1, e.g., portion 24A may be aligned with portion 24B. When the portion of internal tissue 22 engages against the conductor 24 within opening 14, conductor 24 may transition to at least a second configuration or state as illustrated, for example, in FIG. 3, e.g., portion 24B may be bent, flexed, or pressed toward interior surface 20 of cuff 10 by the portion of internal tissue 22. The bias of conductor 24 toward the first configuration or state cause conductor 24 to apply a force against the portion of internal tissue 22 received within opening 14 to maintain contact or engagement of conductor 24 against the portion of internal tissue 22 received within opening 14.

With reference now to FIGS. 4-11, a method for fabricating an implantable cuff electrode is disclosed.

Figure 4:
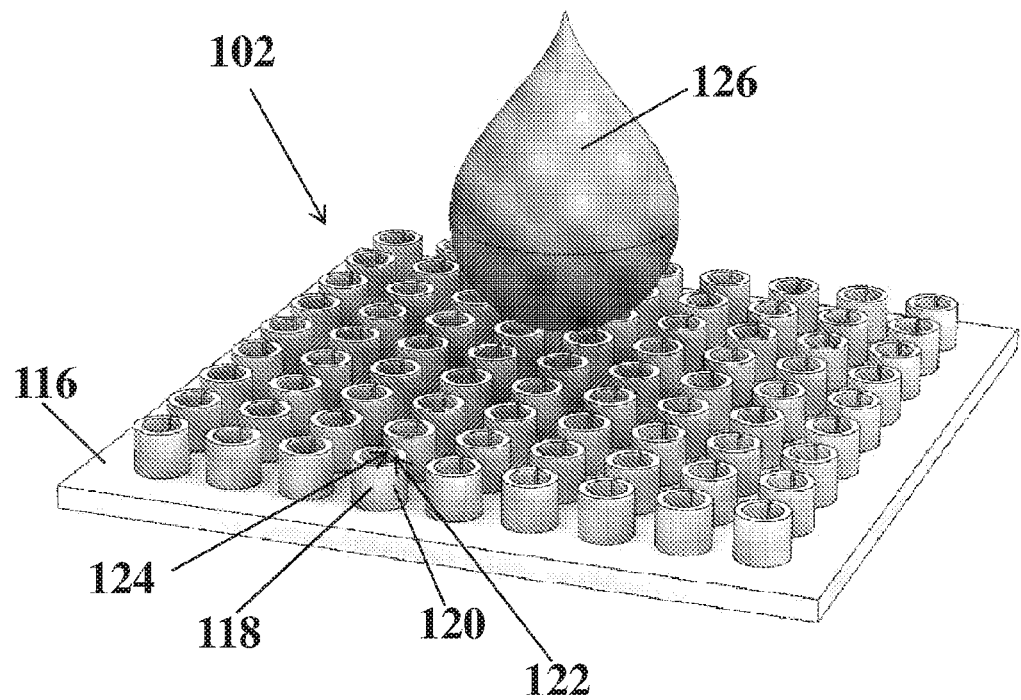
FIG. 4 illustrates a step of a method of fabricating the implantable cuff electrode of FIG. 1 including applying a molding material to a substrate according to an aspect of the present disclosure.

With reference now to FIG. 4, at 102, a patterned mold may be created by applying, e.g., pouring, injecting, etc., a molding material 126 containing an initiator over a silicon substrate 116 patterned with implantable cuff electrode shapes 118. Each cuff electrode shape 118 may include a body 120, an opening 122, and a channel 124. In some aspects, for example, the cuff shapes may be 5 mm×5 mm×8 mm. In some aspects, for example, the openings 122 of the cuff shapes may be less than about 5 mm in a largest dimension. In some aspects, the layer of molding material 126 may be poured to less than about 10 mm in thickness. Other measurements for the cuff shapes and pour thickness may also be used.

Some examples of patterned mold materials that may be used include sugars, waxes, salts, polymers, plasters, epoxies, silicones and rubber. For example, molding material 126 may be a fluorinated elastomer-based material. Some examples of initiators that may be used include photo-, chemical-, thermal-, redox-, persulfates-, ionizing radiation-, electrochemical-, plasma-, ultrasonic-, and any combination thereof.

In some aspects, a poly(dimethylsiloxane) mold may be used to confine the poured molding material to the area of silicon substrate 116.

As the molding material 126 is poured over the silicon substrate 116, the molding material 126 may flow around the cuff electrode shapes 118 and into the openings 122 of the cuff electrode shapes 118 through channels 124. In some aspects, for example, the molding material 126 may be heated to at least a temperature that allows the molding material 126 to be poured over the silicon substrate 116. For example, the temperature may be based on physical properties of the molding material 126 itself. In some aspects, for example, the molding material 126 may be set or cured through thermal, pressure, gas, radiation, light, time, other similar modalities, or any combination thereof.

Once the molding material 126 is poured over the silicon substrate 116, the molding material 126 and silicon substrate 116 are subjected to stimulus matching to the initiator absorbance wavelength for a period of time while under a nitrogen purge. In some aspects, for example, the period of time may be determined based on the physical properties of the molding material 126 and the curing technique that is used. For example, the period of time may be specified by a vendor or manufacturer of the molding material 126 and may be based on a concentration of the molding material 126. When the period of time has expired, the molding material 126 has been fully cured and may be released from the silicon substrate 116 as a mold 128 and placed on a harvest sheet 134 at 104, as illustrated, for example, in FIG. 5. In some aspects, for example, the harvest sheet 134 may be formed of a dissolvable material. In some aspects, harvest sheet 134 may be formed of a non-dissolvable material such as, for example, a metallic or ceramic material. In some aspects, harvest sheet 134 may be separately dissolvable or releasable from molding material 126. In some aspects, harvest sheet 134 may be removable by wet or dry harvesting techniques. In some aspects, mold 128 may be bonded to the harvest sheet 134, for example, by an adhesive, photoinitiator coupling, thermalinitiator coupling, or any combination thereof.

Figure 5:
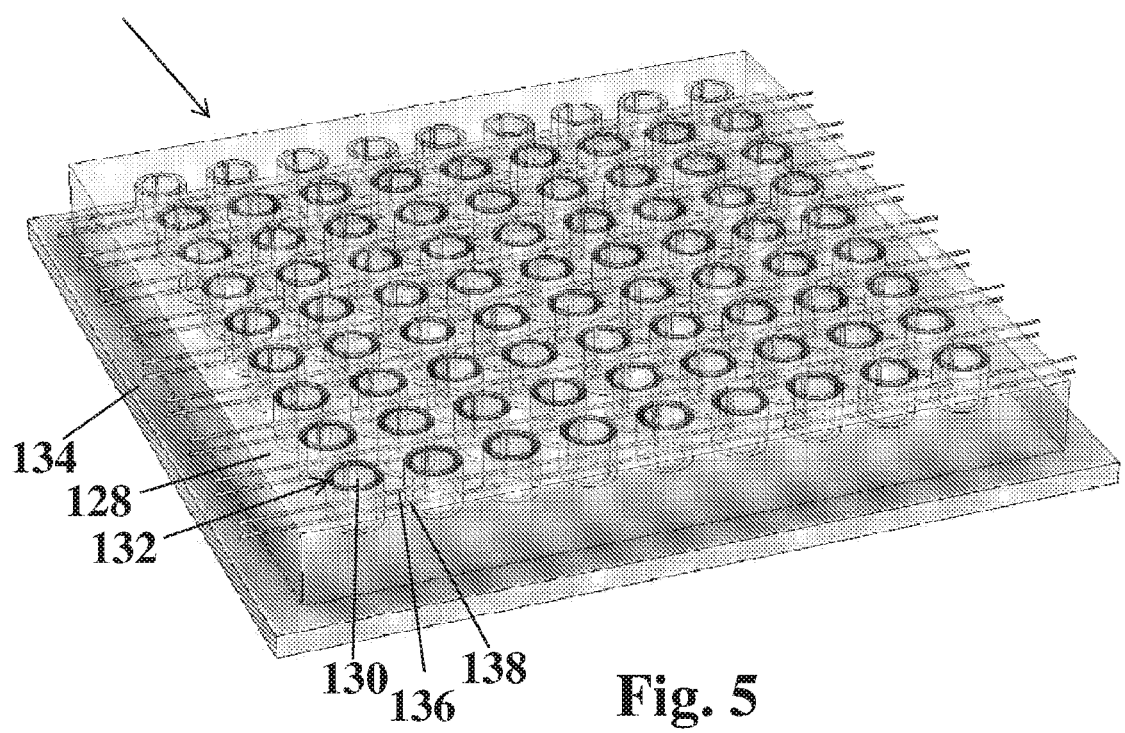
FIG. 5 illustrates a step of a method of fabricating the implantable cuff electrode of FIG. 1 including inserting at least one conductor into a mold according to an aspect of the present disclosure.

With reference now to FIG. 5, mold 128 defines channels 132 in the shape of cuff electrode shapes 118 partially surrounding the portion 130 of the mold 128 that flowed into the openings 122 of the cuff electrode shapes 118.

With continued reference to FIG. 5, at least one conductor may be embedded in the mold 128 through channels 132 and portions 130. For example, conductors 136 and 138 may be embedded through the entire width of mold 128 such that conductors 136 and 138 extend from either end of mold 128. In some aspects, each row of channels 132 in the mold 128 may have at least one conductor embedded therethrough. For example, conductor 136 may be inserted into mold 128 from one side and driven through a number of channels 132, e.g., through all 9 of the channels of the row illustrated in FIG. 5, until the conductor 136 extends from an opposite side of mold 128. Other manners of insertion of conductors 136 and 138 are contemplated where conductors 136 and 138 do not extend all the way through or out of the mold 128. In this manner each channel 132 receives at least one conductor therethrough. In some aspects, for example, each of conductors 136 and 138 may be attached to a guidewire (not shown) that may be inserted through mold 128 to draw the individual conductors 136 and 138 through the mold 128. The guidewire may be subsequently removed once the conductors 136 and 138 are in position.

In some aspects, the at least one conductor may be placed or positioned over the mold 128 on an upper surface, e.g., the surface in which channels 132 are defined, and may be embedded into the upper surface, for example, such that the at least one conductor is received at least partially in a portion at least one of the channels 132.

In some aspects, the at least one conductor may be embedded in the molding material 126 during pouring of the molding material 126 over silicon substrate 116. For example, molding material 126 may be partially poured over silicon substrate 116 and the at least one conductor may be positioned on or embedded in the partially poured molding material 126. In some aspects, for example, molding material 126 may be partially poured between the embedding of each conductor. For example, a first portion of molding material 126 may be partially poured over silicon substrate 116, a first of the conductors may be embedded in the partially poured molding material 126, a second portion of molding material 126 may be partially poured over the embedded first conductor, first portion of molding material 126, and silicon substrate 116, and a second of the conductors may be embedded in the second portion of molding material. A third portion of molding material may be poured over the second conductor, second portion of molding material 126 and silicon substrate to finish the pouring of the molding material 126.

In some aspects, the implantable cuff electrode shapes 118 may include a groove, hole, or channel or similar structure (not shown) for receiving the at least one conductor before or during pouring of the molding material 126 such that the molding material 126 may be poured around the at least one conductor with the at least one conductor extending through the body 120 of the implantable cuff electrode shapes 118. For example, once pouring is complete and the molding material 126 is cured to form mold 128, removal of mold 128 may also remove the at least one conductor from the groove, hole or channel (not shown) of the implantable cuff electrode shapes 118. In some aspects, the implantable cuff electrode shapes 118 may include a structure (not shown), e.g., a flap, teeth, latch, movable wall, or other similar structure, that allows the at least one conductor to be received within the groove, hole, or channel while preventing or inhibiting the molding material 126 from accumulating in the groove, hole or channel (not shown). This may allow the at least one conductor to be embedded in the molding material 126 before or during pouring while still allowing the cuff electrode 150 to be formed in the correct shape.

Figure 6:
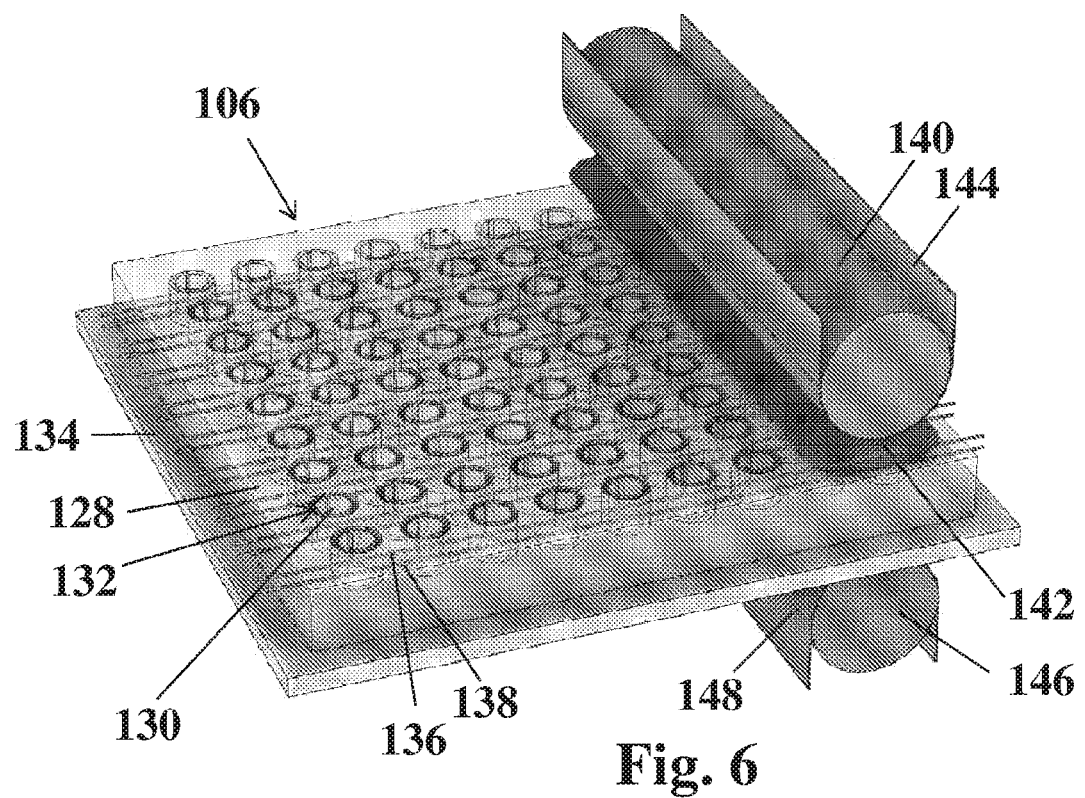
FIG. 6 illustrates a step of a method of fabricating the implantable cuff electrode of FIG. 1 including positioning a material for forming the implantable cuff electrodes on the mold of FIG. 5 and positioning the mold and material for pressing of the material into the mold according to an aspect of the present disclosure.

At 106, with reference now to FIG. 6, a material 142 for forming the implantable cuff electrodes may be prepare as a pure material, solution, or suspension and placed on the mold 128. Example materials that may be prepared may include paralene-C, silicone, Teflon, polyimide, PDMS, SU-8, liquid crystal polymers or other materials as described above. The material 142 may be positioned on or applied to mold 128, and the mold 128 with the material 142 may be positioned or inserted into a molding apparatus or nip roller. The molding apparatus or nip roller may include, for example, a roller 140 that is configured to engage material 142 to press material 142 into the channels 132 to form the implantable cuff electrodes. In some aspects, for example, the nip roller may include roller 140 and a contact surface that may be configured with a fixed separation distance. The nip roller forms a nip-point along a line connecting the center-line of the roller 140 and the contact surface. In some aspects, roller 140 may be heated, driven or non-driven, pressure controlled or fixed pressure, metal surfaces, rubber surfaces, or the like. The temperature of the roller 140 may be set based on specific material properties of the selected material 142.

In some aspects, a film or sheet 144 may be positioned between the roller 140 and the material 142 to protect the roller from contact with or from contaminating the material 142, and to inhibit or prevent the material 142 from sticking to the roller.

In some aspects, the nip roller may include roller 140 and a roller 146 opposite to roller 140 against which harvest sheet 134 may be positioned when roller 140 is engaged against mold 128 to provide a surface against which roller 140 may apply pressure. Rollers 140 and 146 may be configured with a fixed separation distance. In some aspects, for example, one or both of rollers 140 and 146 may be heated, driven or non-driven, pressure controlled or fixed pressure, metal surfaces, rubber surfaces, or the like. In some aspects, the second roller 146 may engage against harvest sheet 134 while roller 140 presses material 142 into the channels 132 of mold 128. In some aspects, a film or sheet 148 may also be positioned between the roller 146 and the harvest sheet 134.

Figure 7:
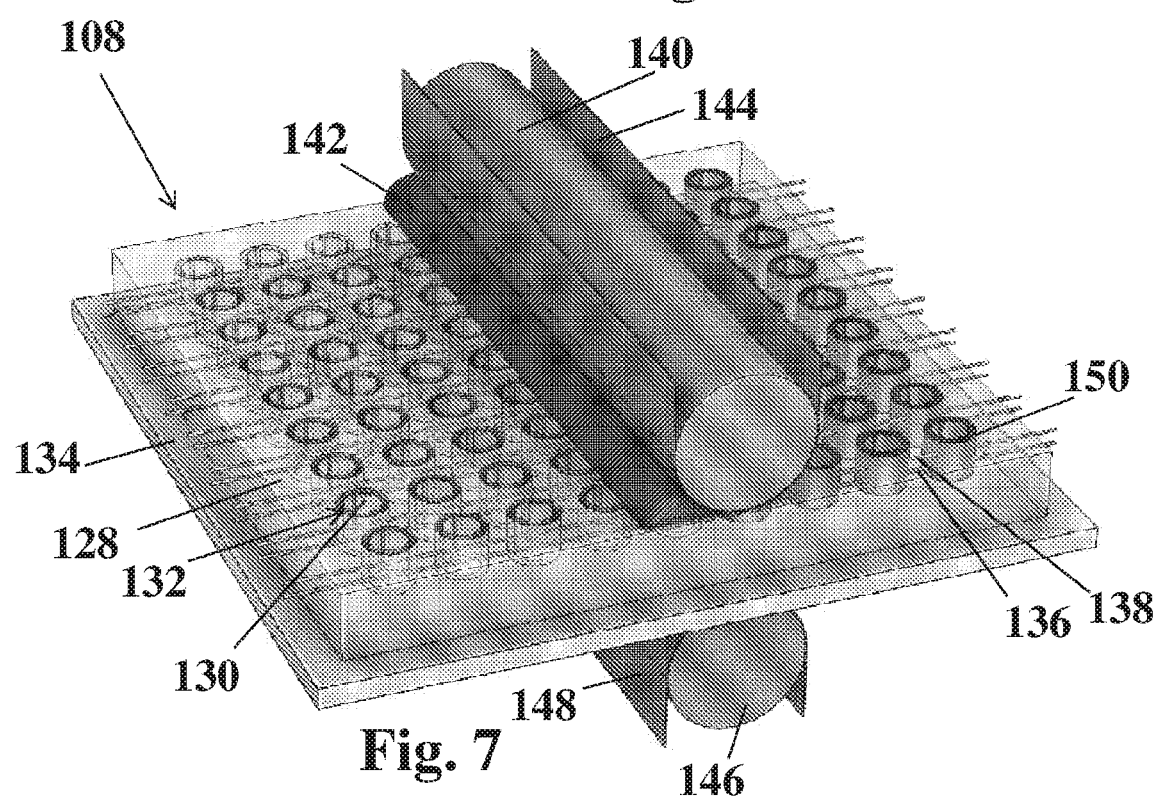
FIG. 7 illustrates a step of a method of fabricating the implantable cuff electrode of FIG. 1 including applying pressure to the material of FIG. 6 to press the material into channels of the mold of FIG. 5 to form implantable cuff electrode bodies.

With reference now to FIG. 7, at 108, mold 128 is fed through the molding apparatus such that roller 140 presses material 142 into channels 132. As seen in FIG. 7, material 142 has entered channels 132 and is formed into the shapes of cuff electrodes 150 by channels 132. Material 142 also flows around the conductors 136 and 138 that extend through the channels 132 such that conductors 136 and 138 may be secured by material 142 when material 142 has been cured. Cuff electrodes 150 may be similar in form and function to cuff electrode 10 described above with reference to FIGS. 1-3 and may include similar components or attributes as described above with respect to cuff electrode 10.

In some aspects, for example, conductors 136 and 138 may be alternatively embedded into mold 128 after material 142 has entered into all of the channels. For example, conductors 136 and 138 may be inserted through the sides of mold 128 and through the material 142 received within channels 132 after material 142 has entered into the channels 132. In some aspects, for example, conductors 136 and 138 may be embedded after material 142 has been cured.

In some aspects, conductors 136 and 138 may be positioned on the upper surface of mold 128 beneath material 142 such that the feeding of mold 128 and material 142 through the molding apparatus may cause the conductors 136 and 138 to be embedded into the channels 132 with the material 142.

Figure 8:
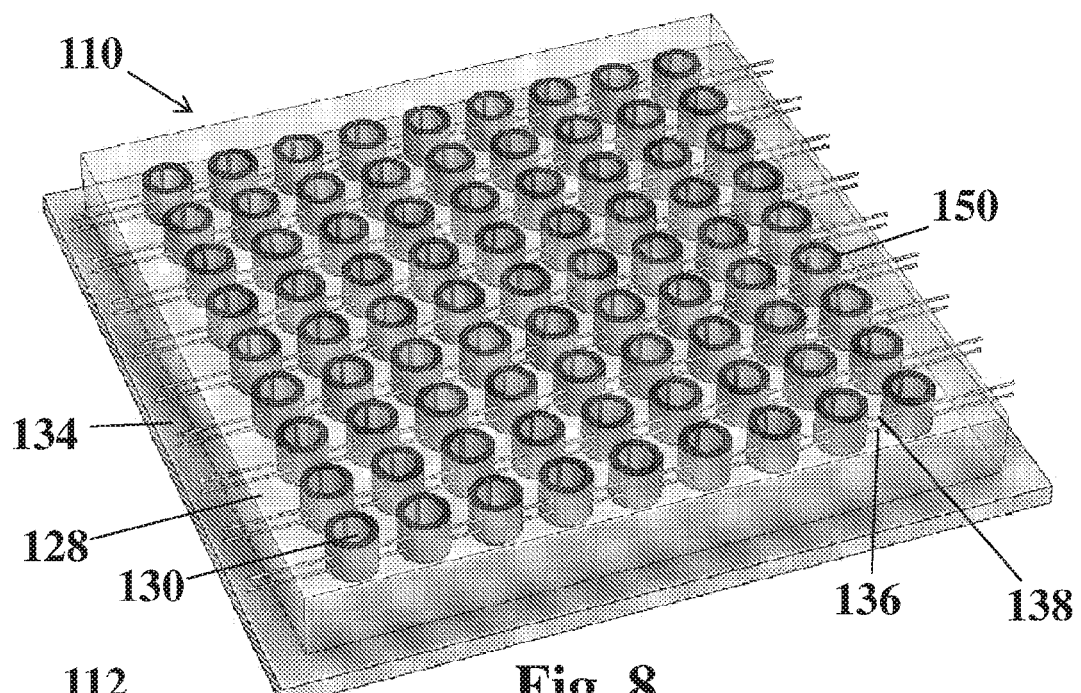
FIG. 8 illustrates the mold of FIG. 5 after the material of FIG. 6 has been pressed into the channels of the mold to form implantable cuff electrode bodies.

With reference now to FIG. 8, at 110, all of the channels 132 have been filled with material 142 by the action of roller 140 (and roller 146 where present) of the molding apparatus to form cuff electrodes 150 with a conductor 136 (and 138 where present) extending through each row. The mold 128 and material 142 are subjected to a curing process, e.g., for a period of time while under a nitrogen purge to harden the cuff electrodes 150.

Figure 9:
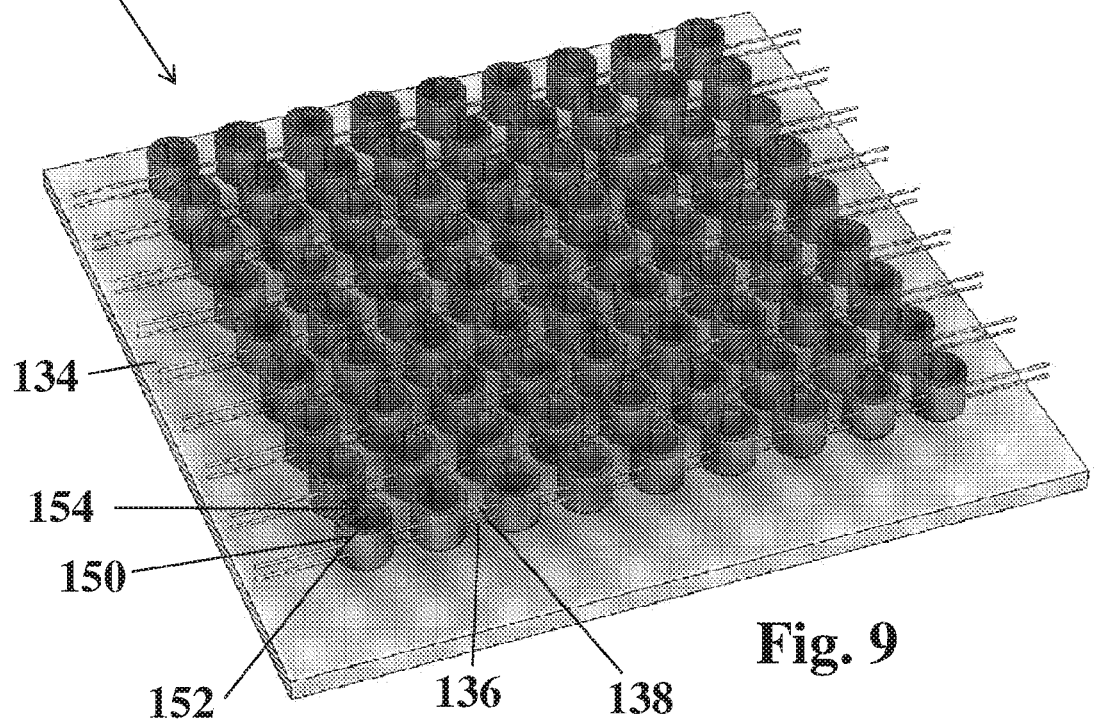
FIG. 9, illustrates a step of a method of fabricating the implantable cuff electrode of FIG. 1 including releasing the implantable cuff electrode bodies of FIG. 8 from the mold.

With reference now to FIG. 9, at 112, mold 128 may be dissolved, for example, using wet harvesting, dry harvesting, or other methods, to release the cuff electrodes 150. For example, mold 128 may be submerged in a solution that dissolves the mold 128 but not the cuff electrodes 150. As seen in FIG. 9, each cuff electrode 150 includes an opening 152 and a channel 154 as described above with reference to implantable cuff 10. At this step, in some aspects, conductors 136 and 138 may still extend through the entire row of cuff electrodes 150.

Figure 10:
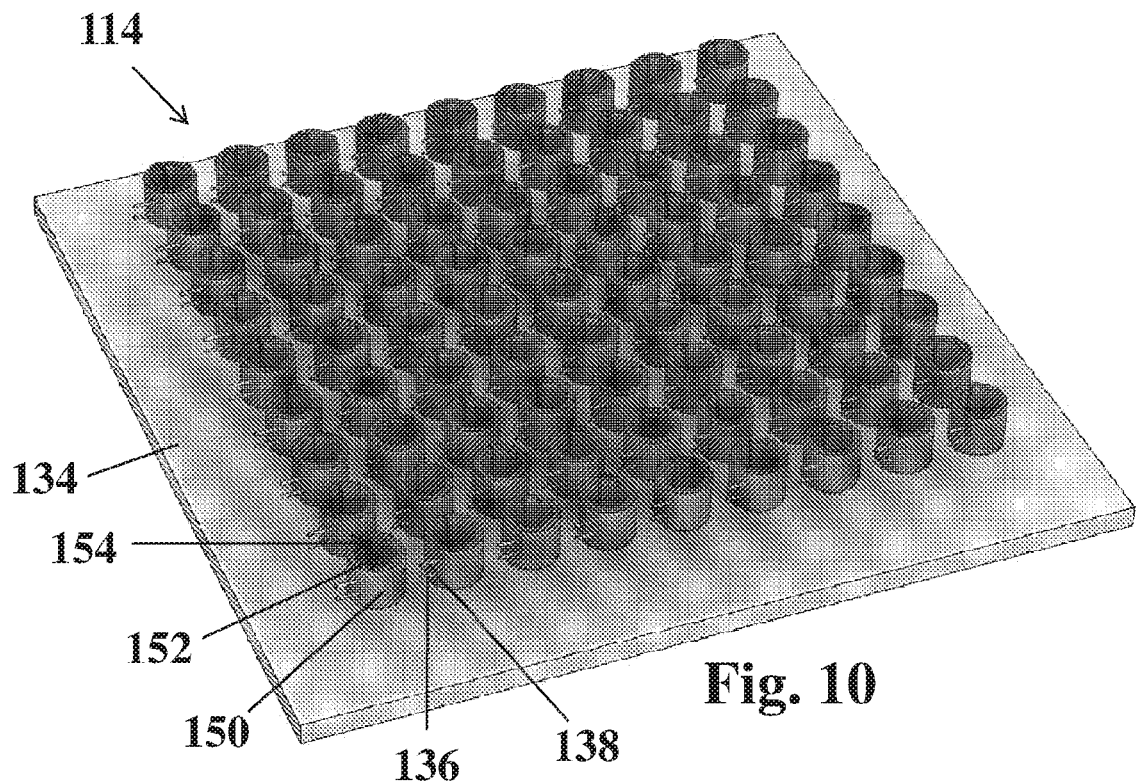
FIG. 10, illustrates a step of a method of fabricating the implantable cuff electrode of FIG. 1 including trimming the conductors for each implantable cuff electrode body of FIG. 9.

With reference now to FIG. 10, at 114, conductors 136 and 138 may be trimmed to a final length (illustrated, for example, in FIGS. 1-3 with reference to example cuff 10) for each cuff electrode 150. For example, in some aspects, conductors 136 and 138 may be trimmed such that they extend from only one portion of an exterior surface of each cuff electrode 150 (e.g., as illustrated in FIG. 1, conductors 24 and 28 extend from exterior surface 18 of cuff 10 on only one side of cuff 10). In some aspects, for example, conductors 136 and 138 may be trimmed flush with the exterior surface of each cuff electrode 150 on another portion or side of the cuff electrode 150 (e.g., as illustrated in FIG. 1, conductors 24 and 28 extend through a portion of exterior surface 18 of cuff 10 on one side of cuff 10 and do not extend from or are flush with a portion of the exterior surface 18 of cuff 10 on an opposing side of cuff 10). In some aspects, conductors 136 and 138 may be mechanically trimmed, for example, by a cutting element. In some aspects, conductors 136 and 138 may be trimmed using a laser cutter. In some aspects, the trimming may be performed manually. In some aspects, the trimming may be performed automatically, for example, by an automated and image guiding cutting mechanism of the sort commonly used in industrial assembly processes. In some aspects, conductors 136 and 138 may be trimmed, e.g., by a laser cutter, prior to the mold 128 being dissolved. In some aspects, for example, conductors 136 and 138 may alternatively be trimmed such that they extend from both sides of each cuff.

In some aspects, conductors 136 and 138 may alternatively be embedded in the formed cuff electrodes 150 after the cuff electrodes have been released from the mold 128. For example, the cuff electrodes 150 may be formed as described above with no embedded conductors and the conductors may later be embedded in each cuff electrode 150 after the cuff electrodes 150 are released from the mold 128. In some aspects, no trimming may be necessary if the conductors are embedded after the cuff electrodes 150 are released from the mold 128.

In some aspects, as an alternative to embedding electrodes into the cuff electrodes 150, each cuff electrode may have conducting elements deposited thereon, for example on an interior surface (e.g., surface 20 of cuff 10 illustrated in FIG. 1) using sputtering, dipping or other similar techniques. For example, interior surface 20 may be coated with conducting elements to form a conductor. In some aspects, one or more conducting leads may be attached or welded to the conducting elements.

Figure 11:
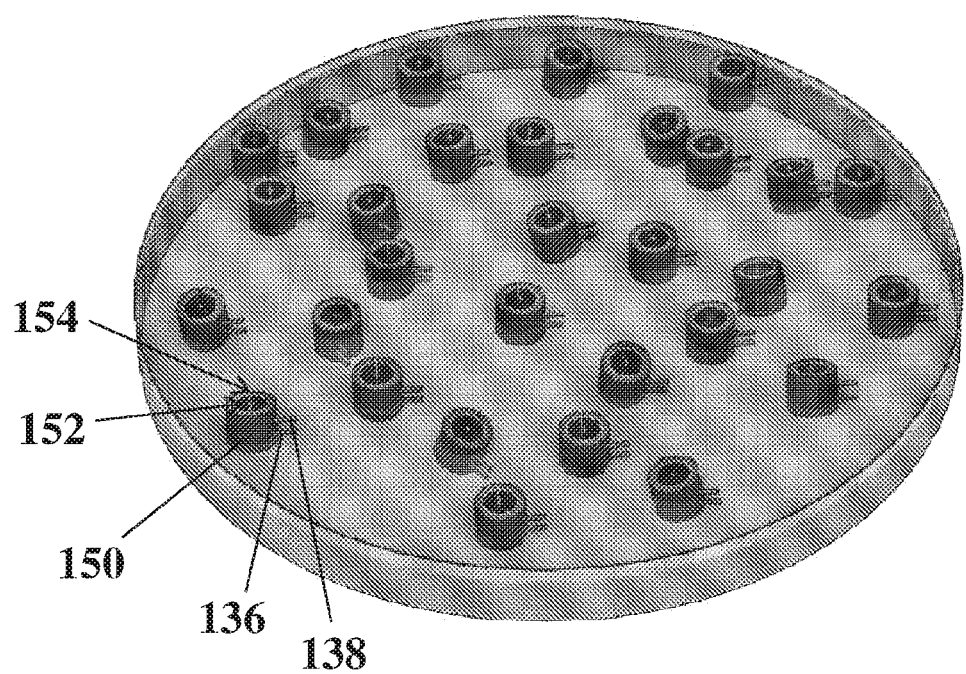
FIG. 11 illustrates the fabricated implantable cuff electrodes of FIG. 10, released from a supporting harvest sheet.

With reference now to FIG. 11, at 116, fabrication of the electrode cuffs 150 may be completed by dissolving or peeling off harvest sheet 134 to release the electrode cuffs 150. As seen in FIG. 11, each individual electrode cuff 150 may include an opening 152, channel 154, and at least one conductor 136, 138 and may function in a similar manner or have similar features as cuff 10 as described above with reference to FIGS. 1-3. Electrode cuffs 150 are now ready for use.

In some aspects, a method for fabricating an implantable cuff electrode may include providing a layer of fluorinated elastomer-based material. The layer of fluorinated elastomer-based material may include a first surface defining a plurality of cavities, wherein each cavity of the plurality of cavities may have a predetermined shape and may be less than about 5 millimeters in a largest dimension. In some aspects, the layer of fluorinated elastomer-based materials may be less than about 10 millimeters in thickness.

In some aspects, a support layer may be bonded to a second surface of the layer of fluorinated elastomer-based material opposite the first surface.

In some aspects, a sheet may be positioned to face the first surface of the layer of fluorinated elastomer-based material.

In some aspects, a curable material may be disposed between the sheet and the first surface of the layer of fluorinated elastomer-based material. The curable material may be configured to conform to the cavities of the first surface.

In some aspects a first roller and a second roller defining a nip point to receive the layer of fluorinated elastomer-based material bonded to the support layer, the sheet, and the material may be defined and dimensioned.

In some aspects, the layer of fluorinated elastomer-based material bonded to the support layer, the sheet, and the material may be conveyed through the first roller and second roller to form a molded cuff and an electrode may be embedded into the cuff to form a cuff electrode either before or after the material is conveyed through the first and second rollers.

In some aspects, the method for fabricating an implantable cuff electrode for encircling internal body tissue may further include disposing a tie-layer between the layer of fluorinated elastomer-based material and the support layer to attach the support layer.

In some aspects, the layer of fluorinated elastomer-based materials may be attached to the support layer by photoinitiator coupling and thermalinitiator coupling.

In some aspects, the first roller and second roller may be configured and dimensioned to pinch the layer of fluorinated elastomer-based material, the support layer, the sheet, and the material.

In some aspects, the cuff electrode may include a body member having at least one electrode being partially captively held in the body member and providing a contact area of the at least one electrode. In some aspects, the cuff electrode may include means for interfacing the contact area of the at least one electrode with the captively held body tissue. In some aspects, the means for interfacing the contact area of the at least one electrode includes means for providing an electrical contact to the cuff electrode. In some aspects, the means for interfacing the contact area of the at least one electrode includes means for retaining the captively held body tissue, the means for retaining the captively held body tissue selected from the group consisting of a flap, a door, a pin, a clip, and a press-button.

In some aspects, at least one electrode the at least one electrode is a conducting polymer. In some aspects, the at least one conducting polymer electrode includes the means for elucidating the diameter of the captively held body tissue. In some aspects, the means for elucidating the diameter of the captively held body tissue when the at least one electrode is a conducting polymer, where changes in the diameter of the captively held body tissue induce a measurable electrical property change in the at least one conducting polymer electrode.

In some aspects, a method for neural stimulation and recording using an implantable cuff with the cuff having at least one conducting polymer electrode.

In some aspects, the implantable cuff having at least one conducting polymer electrode with at least one electrode making contact with the captively held body tissue.

In some aspects, the at least one conducting polymer electrode is in contact with the captively held body tissue wherein a change in diameter of the tissue exerts a force on the at least one electrode causing a relative change an electrical property change of the at least one electrode.

In some aspects, the electrical property change of the at least one conducting polymer electrode is related to changes in the captively held tissue body selected from the group consisting of inflammation, denervation and pulsation.

In some aspect, a replica printing method for fabricating an implantable cuff electrode is provided including the steps of: providing a layer of fluorinated elastomer-based material that is less than about 10 millimeters in thickness, the layer including a first surface (in one embodiment a top surface) defining a plurality of cavities, wherein each cavity of the plurality of cavities has a predetermined shape and is less than about 5 millimeters in a largest dimension, bonding a support layer to a second surface of the layer of fluorinated elastomer-based material opposite the first surface in one embodiment a bottom surface, positioning a sheet to face the first surface of the layer of fluorinated elastomer-based material, disposing a curable material between the sheet and the first surface of the layer of fluorinated elastomer-based material, configuring the curable material to conform to the cavities of the first surface and providing a first roller and a second roller defining a nip point wherein the nip point is configured and dimensioned to receive the layer of fluorinated elastomer-based material bonded to the support layer, the sheet, and the material.

In some aspects, another method for fabricating an implantable cuff electrode for contacting or encircling internal body tissue is disclosed, including the steps of fabricating a body member from formable material, forming in said body member a channel, sizing said channel to have an interior size greater than said outside diameter of said internal body tissue and positioning within said channel at least one electrode element wherein said at least one electrode is situated to make contact with said body tissue.

In some aspects, another method for fabricating an implantable cuff electrode for contacting or encircling internal body tissue is disclosed where the body member is created of a formable material. The body member may have a channel sized to have an interior size greater than an outside diameter of the internal body tissue. The body member may have at least one electrode element positioned in the channel and situated to be able to make contact with the body tissue when the body tissue is received within the channel.

In some aspects, another method for fabricating an implantable cuff electrode for contacting or encircling internal body tissue is disclosed. The implantable cuff electrode may include a body member and at least one electrode. The at least one electrode may be partially captively held in the body member and may provide a contact area for contacting internal body tissue received within an opening or channel of the body member. The implantable cuff electrode may include means for interfacing the contact area of the at least one electrode being partially captively held in the body member with the captively held body tissue, for example, by engagement of the electrode, e.g., conductor 20, against the captively held body tissue as described above with reference to FIG. 3.

Although specific aspects of the invention have been described, it will be understood by those of skill in the art that there are other aspects that are equivalent to the described aspects. Accordingly, it is to be understood that the aspect is not to be limited by the specific illustrated aspects, but only by the scope of the appended claims.

What is claimed:

1. A method for fabricating an implantable cuff electrode comprising:
   preparing a substrate comprising an implantable cuff electrode shape;
   applying a mold material to the substrate;
   curing the mold material to form a mold, the mold comprising a channel defined by the implantable cuff electrode shape of the substrate;
   releasing the mold from the substrate;
   inserting at least one conductor into the mold, the at least one conductor penetrating through the channel of the mold;
   pressing a formable material into the channel of the mold to form a body of an implantable cuff electrode, the body formed about the at least one conductor penetrating through the channel of the mold;
   curing the body of the implantable cuff electrode; and
   releasing the body of the implantable cuff electrode from the mold,
   wherein the body of the implantable cuff electrode is formed with an opening extending therethrough, the opening configured to receive a portion of internal body tissue therethrough.

2. The method of claim 1, wherein the formable material is pressed into the channel by at least one roller.

3. The method of claim 2, wherein the at least one roller is heated.

4. The method of claim 1, wherein the portion of internal body tissue that the opening is configured to receive is selected from the group consisting of nerves, smooth muscles, striated muscles, arteries, veins, ligamental tissues, connective tissues, cartilage tissues, bones, or other similar body tissues, structures and organs.

5. The method of claim 1, wherein the body of the implantable cuff electrode is formed with a channel extending from an exterior surface of the body into the opening, the channel of the body configured to allow passage of the portion of internal body tissue therethrough to the opening.

6. The method of claim 1, wherein a cross-sectional region of the opening defines a shape selected from the group consisting of a circular shape, an oval shape, a triangular shape, a pentagonal shape, a square shape, a rectangular shape, a star shape, and a hexagonal shape.

7. The method of claim 1, wherein a cross-sectional region of the opening has a diameter between about 0.001 mm and about 12 mm.

8. The method of claim 7, wherein the cross-sectional region of the opening has a diameter between about 0.01 mm and about 10 mm.

9. The method of claim 8, wherein the cross-sectional region of the opening has a diameter between about 0.1 mm and about 10 mm.

10. The method of claim 9, wherein the cross-sectional region of the opening has a diameter between about 0.5 mm and about 10 mm.

11. The method of claim 1, wherein the opening is shaped such that the outer surface of the opening contacts the internal body tissue.

12. The method of claim 1, wherein the formable material is a high volume resistivity material having a resistivity greater than about $1 \times 10^{22}$ Ω-cm.

13. The method of claim 1, wherein the formable material is a material selected from the group consisting of paralene-C, silicone, Teflon, polyimide, PDMS, SU-8 and liquid crystal polymers.

14. The method of claim 1, wherein the cured body of the implantable cuff electrode has a flexural rigidity of less than about $1 \times 10^{-12}$ N-m$^2$.

15. The method of claim 1, wherein the at least one conductor is selected from the group consisting of titanium nitride, platinum, platinum-iridium alloys, gold, hydrogel, iridium oxide, silicon carbide, stainless steel and graphene, carbon fibers, carbon nanotube structures, Tantalum, $Ta_2O_5$, PEDOT and conducting polymers.

* * * * *